(12) United States Patent
Bennett et al.

(10) Patent No.: US 6,481,679 B1
(45) Date of Patent: Nov. 19, 2002

(54) SYSTEM FOR MOUNTING MEDICAL ACCESSORIES ON SUPPORTIVE STRUCTURES

(76) Inventors: Bryant K. Bennett, 1108 S. Edgefield, Dallas, TX (US) 75208; Robert K. Bennett, 1108 S. Edgefield, Dallas, TX (US) 75208

( * ) Notice: Subject to any disclaimer, the term of this patent is extended or adjusted under 35 U.S.C. 154(b) by 0 days.

(21) Appl. No.: 09/714,918

(22) Filed: Nov. 17, 2000

(51) Int. Cl.[7] .............................................. F21V 35/00
(52) U.S. Cl. ........................ 248/224.51; 248/223.41; 248/224.61
(58) Field of Search ..................... 248/224.51, 223.41, 248/224.61, 222.13, 229.25, 230.6

(56) References Cited

U.S. PATENT DOCUMENTS

| | | | | |
|---|---|---|---|---|
| 1,495,189 A | * | 5/1924 | Mack | 248/224.5 |
| 2,696,963 A | | 12/1954 | Shepherd | |
| 2,939,364 A | * | 6/1960 | Doswell et al. | 88/81 |
| D221,366 S | * | 8/1971 | Saternus | D83/1 |
| 3,709,372 A | | 1/1973 | Alexander | |
| 3,734,439 A | * | 5/1973 | Wintz | 248/224 |
| 3,881,677 A | * | 5/1975 | Ihlenfeld | 248/311 |
| 4,176,580 A | * | 12/1979 | Gallegos | 84/327 |
| 4,620,736 A | | 11/1986 | Shanks | |
| 4,700,922 A | | 10/1987 | Gross | |
| 5,086,958 A | | 2/1992 | Nagy | |
| 5,149,036 A | | 9/1992 | Sheehan | |
| 5,288,093 A | | 2/1994 | Gross | |
| 5,356,105 A | | 10/1994 | Andrews | |
| 5,615,854 A | * | 4/1997 | Nomura et al. | 248/287.1 |
| 5,829,723 A | * | 11/1998 | Brunner et al. | 248/222.13 |
| D437,639 S | * | 2/2001 | Breda et al. | D24/128 |
| 6,305,559 B1 | * | 10/2001 | Hardy | 211/184 |

* cited by examiner

Primary Examiner—Kimberly Wood

(57) ABSTRACT

A system is provided for mounting medical accessories on support structures that includes a female mounting component for mounting to a supportive structure and a male mounting component for mounting to a medical accessory. The female mounting component includes a receiver assembly comprising a base member and a pair of opposed channel members on the base member to form a receptive channel, which has upper and lower ends and a transverse dimension decreasing from the upper to lower ends. The female mounting component includes a first mounting structure attached to the receiver assembly. The male mounting component comprises an insertion member removably insertable into the receptive channel of the female mounting component at the upper end thereof. The insertion member has upper and lower ends and a transverse dimension that decreases from the upper to lower ends. The male mounting component includes a second mounting structure attached to the insertion member. Optionally, the second mounting structure comprises a bag hanger structure for supporting a fluid-holding bag. Optionally, the first mounting structure may comprise a bracket mounting structure for mounting the receiver assembly to a bar supportive structure, a clamp mounting structure adapted for mounting the receiver assembly to a bar supportive structure, or a track mounting structure for mounting the receiver assembly to a track. Optionally, a pair of the receiver assemblies may be coupled together such that the receptive channels of the receiver assemblies are oriented in opposite directions.

9 Claims, 4 Drawing Sheets

SYSTEM FOR MOUNTING MEDICAL ACCESSORIES ON SUPPORTIVE STRUCTURES

BACKGROUND OF THE INVENTION

1. Field of the Invention

The present invention relates to medical accessory mounting systems and more particularly pertains to a new system for mounting medical accessories on supportive structures for providing a uniform system of quickly and conveniently mounting a variety of different medical accessories on a variety of different support structures.

2. Description of the Prior Art

Medical accessories, such as intravenous (IV) fluid supply bags and fluid pumps, are typically supported on an IV support post adjacent to a patient being treated with the IV fluids. The IV support post is usually mounted on a wheeled base that permits the support post (and the items supported on the post) to be moved with the patient as the patient is moved between locations in a treatment institution. The patient is often supported on a bed, stretcher or wheelchair, especially when the patient is being transported between locations. The IV support post is usually rolled on its wheeled base with the bed, stretcher, or wheelchair supporting the patient.

The movement of the IV support post presents a number of difficulties, one of the most vexing being the top heaviness of the support post when an IV fluid bag is suspended from the top of the support post and an IV fluid pump is also mounted on the post. The support post is thus very vulnerable to tipping, which can strike the patient or care personnel, or even pull the IV tubing and needle from the body of the patient. The wheels on the base of the post only exacerbate the tipping problem. To counter the tendency to tip, the base of the IV support post has a plurality of legs radiating outward from the post to wide the supportive base of the support post. However, the radiating legs of the base pose a tripping hazard, and this makes the support post difficult to move through doors of rooms and elevators at the same time as (or in close proximity to) the bed, stretcher, or wheelchair of the patient. As a result, additional care personnel are often employed to transport the IV support post or posts along with the personnel just dedicated to transporting the patient.

The use of IV support posts thus have presented a safety problem to patients being transported, as well as stationary patients, and also to care personnel. However, any solution to this problem must permit easy mounting and dismounting of the medical devices on conventional support structures for supporting the medical devices, such as existing IV support posts, as well as patients support structures such as patient beds, stretchers, wheelchairs and the like.

SUMMARY OF THE INVENTION

In view of the foregoing disadvantages inherent in the known types of medical accessory mounting systems now present in the prior art, the present invention provides a new system for mounting medical accessories on supportive structures construction wherein the same can be utilized for providing a uniform system of quickly and conveniently mounting a variety of different medical accessories on a variety of different support structures.

The general purpose of the present invention, which will be described subsequently in greater detail, is to provide a new system for mounting medical accessories on supportive structures apparatus and method which has many of the advantages of the medical accessory mounting systems mentioned heretofore and many novel features that result in a new system for mounting medical accessories on supportive structures which is not anticipated, rendered obvious, suggested, or even implied by any of the prior art medical accessory mounting systems, either alone or in any combination thereof.

To attain this, the present invention generally comprises a female mounting component for mounting to a supportive structure and a male mounting component for mounting to a medical accessory. The female mounting component comprises a receiver assembly for removably receiving the insertion member. The receiver assembly comprises a base member and a pair of opposed channel members mounted on the base member to form a receptive channel. The receptive channel has an upper end and a lower end, with the receptive channel having a transverse dimension that decreases from the upper end of the receptive channel toward the lower end of the receptive channel. The female mounting component includes a first mounting structure attached to the receiver assembly for mounting the receiver assembly on a supportive structure. The male mounting component comprises an insertion member removably insertable into the receptive channel of the female mounting component at the upper end thereof. The insertion member has an upper end and a lower end, with the upper end and the lower end each having a transverse dimension that decreases from the upper end toward the lower end. The male mounting component includes a second mounting structure attached to the insertion member for mounting the insertion member on a medical accessory. Optionally, the second mounting structure comprises a bag hanger structure for supporting a fluid-holding bag. Optionally, the first mounting structure may comprise a bracket mounting structure for mounting the receiver assembly to a bar supportive structure, a clamp mounting structure adapted for mounting the receiver assembly to a bar supportive structure, or a track mounting structure for mounting the receiver assembly to a track. Optionally, a pair of the receiver assemblies may be coupled together such that the receptive channels of the receiver assemblies are oriented in opposite directions.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The various features of novelty which characterize the invention are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description make reference to the annexed drawings wherein.

DESCRIPTION OF THE PREFERRED EMBODIMENT

Figure 1:
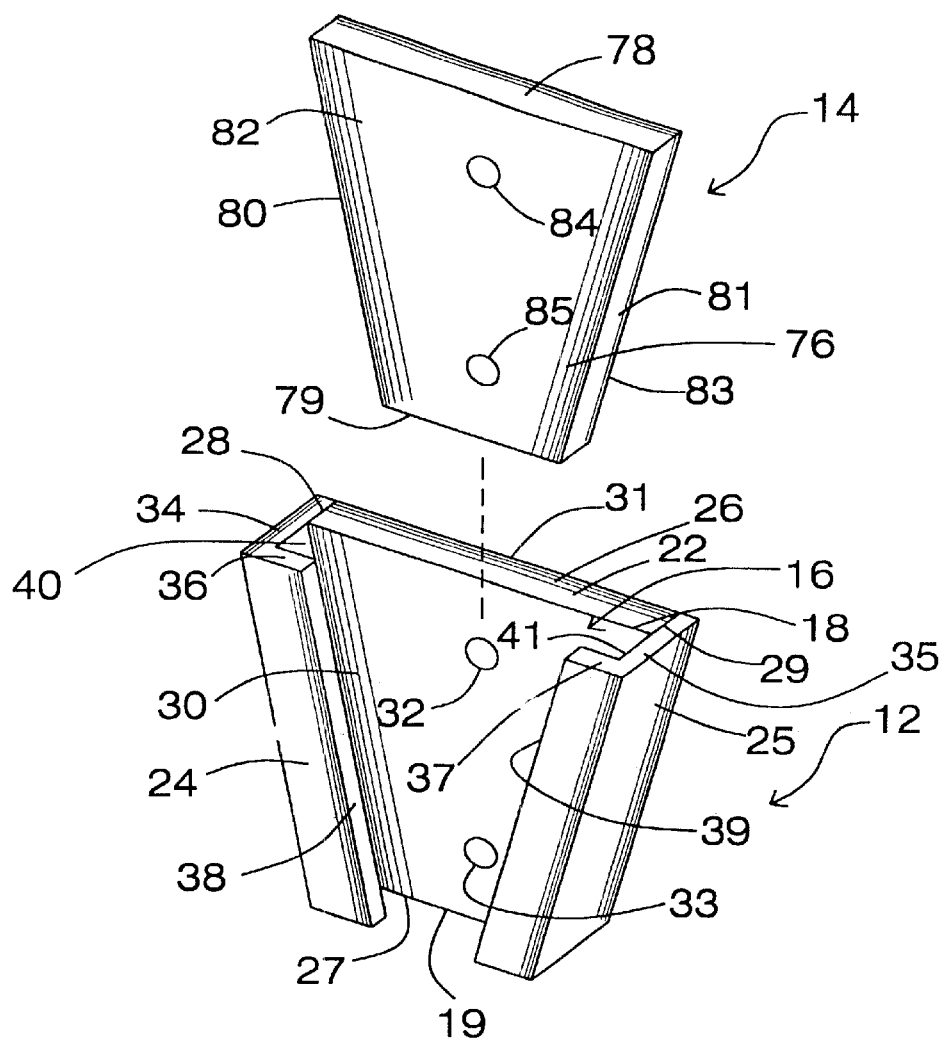
FIG. 1 is a schematic perspective view of portions of the male and female mounting components of the system of the present invention shown in a disengaged, exploded relationship.
Figure 2:
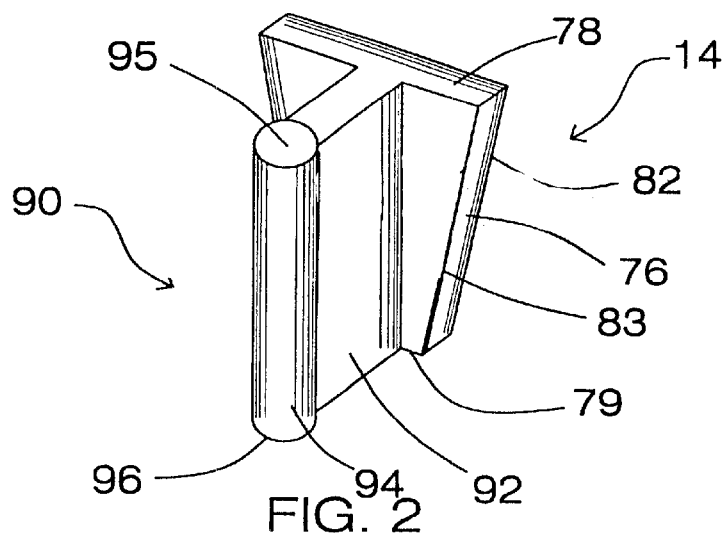
FIG. 2 is a schematic perspective of one aspect of the male mounting component of the present invention having the insertion member combined with the post structure.

With reference now to the drawings, and in particular to FIGS. 1 through 8 thereof, a new system for mounting medical accessories on supportive structures embodying the principles and concepts of the present invention and generally designated by the reference numeral 10 will be described.

As best illustrated in FIGS. 1 through 8, the system 10 of interchangeable mountings for removably mounting a medical accessory on a supportive structure generally comprises a female mounting component 12 for mounting to a supportive structure and a male mounting component 14 for mounting to a medical accessory such that the medical accessory is supported on the supportive structure. Significantly, a plurality of adaptive structures are provided for securely and integrally mounting the female and male mounting components to the respective supportive structures and medical accessories for the purpose that substantially all supportive structures and medical accessories in a care facility may be provided with complementary mounting structures.

The female mounting component 12 of the invention defines a receptive channel 16 (see FIG. 1). The receptive channel 16 has an upper end 18 and a lower end 19. The receptive channel 16 has a width that decreases from the upper end toward the lower end for blocking movement of the insertion member completely through the receptive channel. The female mounting component includes a receiver assembly 20 that forms the receptive channel 16 for removably receiving the insertion member of the male mounting member.

The receiver assembly preferably comprises a base member 22 and a pair of opposed channel members 24, 25 mounted on the base member to form the receptive channel 16. The base member 22 has an upper end 26 and a lower end 27, and a pair of sides 28, 29 extending between the upper and lower ends. The upper end 26 and the lower end 27 each have a transverse dimension, with the transverse dimension of the upper end being greater than the transverse dimension of the lower end. The sides of the base member converge toward the lower end and diverge toward the upper end. The sides 28, 29 are preferably substantially straight, and the upper and lower ends are also preferably substantially straight. In one highly preferred embodiment of the of the invention, the transverse dimension of the lower end is approximately half of the transverse dimension of the upper end. The base member 22 has front face 30 and a rear face 31. The front 30 and rear 31 faces may be substantially parallel. Ideally the base member comprises a plate of a rigid and strong material, such as aluminum.

A first mounting hole 32 may be formed in the base member and a second mounting hole 33 may be formed in the base member for receiving fasteners to mount the base member on the first mounting structure. The first and second mounting holes may be located on a line extending between a midpoint of the upper and lower ends of the base member.

The channel members 24, 25 are each mounted on one of the sides 28, 29 of the base member 22. Each of the channel members 24, 25 has a first arm 34, 35 mounted on the side of the base member and a second arm 36, 37 extending substantially parallel to the front face of the base member. Preferably, the first arm is oriented substantially perpendicular to the second arm. The second arm is spaced from the front face of the base member, and preferably extends substantially parallel to the front face 30 of the base member. The second arm 36 of a first one 24 of the channel members is spaced from the second arm 37 of a second one 25 of the channel members. The second arms 36, 37 of the channel members converge toward each other toward the lower end 27 of the base member to form the receptive channel. Each of the second arms 36, 37 has an inward edge 38, 39, and the inward edges of the second arms are preferably substantially linear and smooth. The first arms 34, 35 of the channel members each have an inner surface 40, 41.

The female mounting component 12 further includes a first mounting structure attached to the receiver assembly for mounting the receiver assembly on a supportive structure. Significantly, the configuration of the first mounting structure may be varied depending upon the nature of the supportive structure to be engaged by the first mounting structure.

Figure 4:
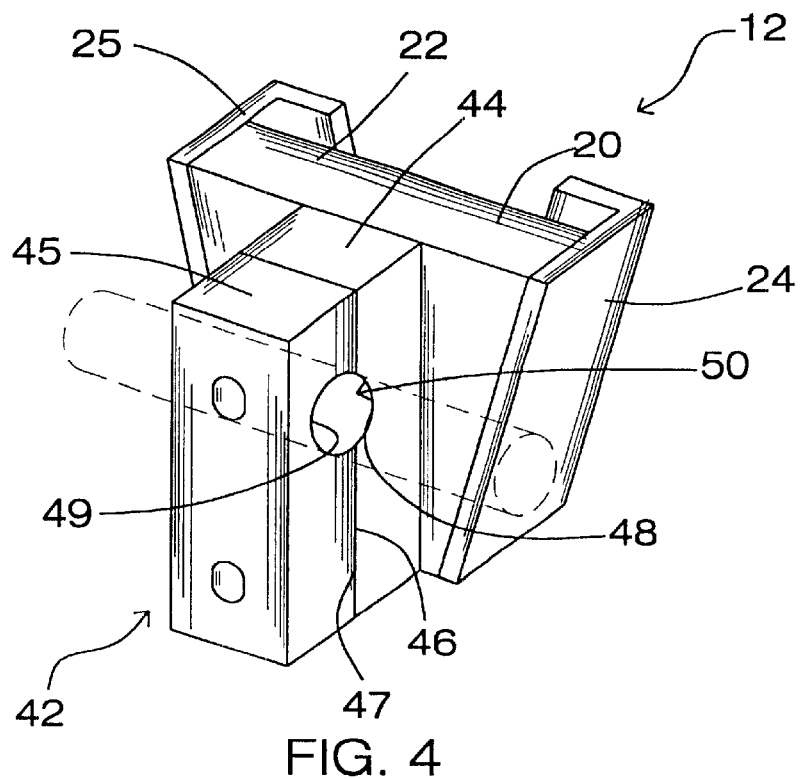
FIG. 4 is a schematic perspective view of one aspect of the female mounting component of the present invention having the receiver assembly combined with the bracket mounting structure.

Optionally, the first mounting structure may comprise a bracket mounting structure 42 for mounting the receiver assembly to a bar supportive structure, such as a horizontally oriented bar (see FIG. 4). The bracket mounting structure comprises an inner member 44 and an outer member 45. The inner member 44 is mounted on the rear face 31 of the base member 22. The inner 44 and outer 45 members each have an inner face 46, 47. The inner face 46 of the inner member is oriented toward the inner face 47 of the outer member. The inner faces 46, 47 of the inner and outer members each have a channel 48, 49 formed therein. Together, the channels form a passage 50 for receiving a bar of a supporting structure such as a wheelchair or a hospital bed. The outer member 45 is mounted on the inner member 44 by a fastening structure. The fastening structure permits adjustment of the distance between the inner faces 46, 47 of the inner 44 and outer 45 members to thereby adjust the size of the passage 50 for adapting to the size of the bar and applying gripping force on the bar for securing the positions of the inner and outer members on the bar. The fastening structure may comprise a pair of fasteners extending through the outer member and into the inner member.

Figure 5:
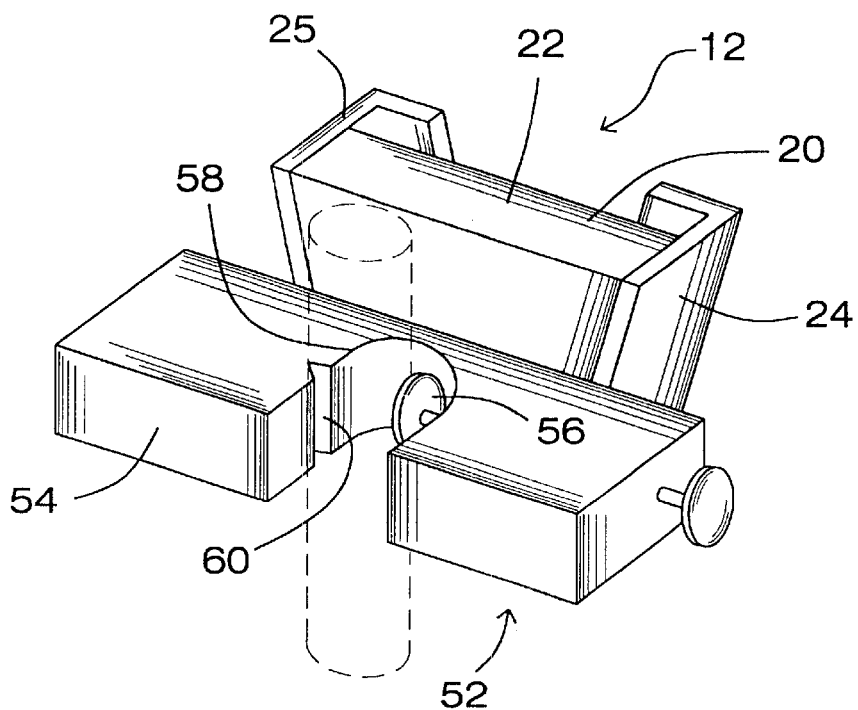
FIG. 5 is a schematic perspective view of one aspect of the female mounting component of the present invention having the receiver assembly combined with the clamp mounting structure.

Optionally, the first mounting structure may comprise a clamp mounting structure 52 adapted for mounting the receiver assembly 20 to a bar supportive structure, such as a vertically oriented bar (see FIG. 5). The clamp mounting structure 52 comprises a clamp member 54 and a pinching member 56 mounted on the clamp member. The clamp member 54 is mounted on the rear face 31 of the base member. The clamp member defines a pinching channel 58 therein for receiving a portion of a bar. The pinching member 56 extends into the pinching channel 58. The pinching member 56 is advanceable into the pinching channel to releasably engage a bar positioned in the pinching channel. The pinching member is preferably threadedly mounted on the clamp member such that rotation of the pinching member advances the pinching member into the pinching channel. A notch 60 is formed in the pinching channel at a location that permits the pinching member to be advanced toward the notch for pressing a bar toward the notch.

Figure 6:
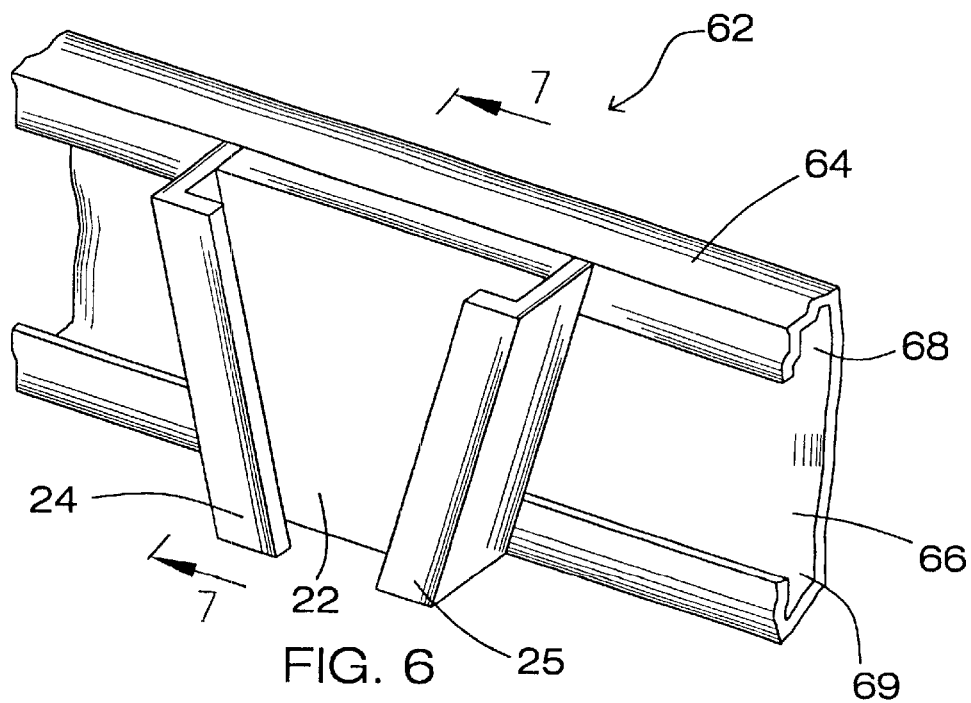
FIG. 6 is a schematic perspective view of one aspect of the female mounting component of the present invention having the receiver assembly combined with the track mounting structure.
Figure 7:
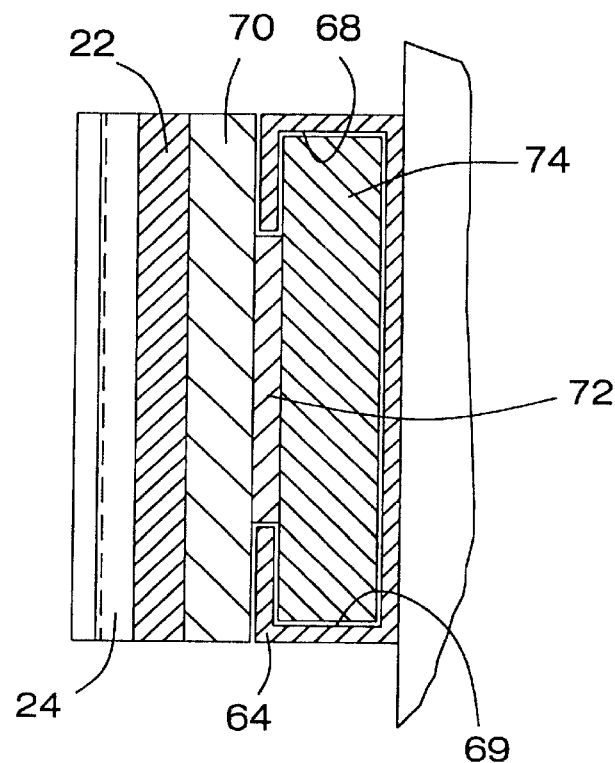
FIG. 7 is a schematic sectional view of the receiver assembly combine with the track mounting structure taken along line 7—7 in FIG. 6.

Optionally, the first mounting structure may comprise a track mounting structure 62 for mounting the receiver assembly to a track 64 (see FIGS. 6 and 7). The track 64 comprises a channel 66 with a pair of opposed slots 68, 69. The track mounting structure comprises an interface plate 70 for mounting to the rear face 31 of the base member, a middle plate 72 mounted on the interface plate, and a slide plate 74 mounted on the middle plate. The middle plate 72 may have a width that is less than a width of the slide plate to form a pair of oppositely oriented grooves. The slide plate 74 is adapted to be inserted into and slide along the channel of the track. The slide plate 74 has a pair of spaced parallel sides for engaging the opposed slots of the track.

The male mounting component 14 of the invention is removably insertable into the receptive channel of the female mounting component at the upper end thereof. The male mounting component includes an insertion member 76 (see FIG. 1). The insertion member 76 has an upper end 78 and a lower end 79, and a pair of sides 80, 81 extending between the upper and lower ends. The upper 78 and lower 79 ends each have a transverse dimension. The transverse dimension of the upper end is greater than the transverse dimension of the lower end so that the sides converge toward the lower end and diverge toward the upper end. The sides 80, 81 of the insertion member are preferably substantially straight, and the upper and lower ends are also preferably substantially straight. The transverse dimension of the lower end is approximately half of the transverse dimension of the upper end. Preferably, the size and shape of the insertion member 74 is substantially the same as the size and shape of the base member 22 of the receiver assembly 20 such that insertion member is easily positionable adjacent to the base member and between the channel members 24, 25. The insertion member 76 has front 82 and rear 83 faces. The front and rear faces each may be substantially planar, and may be oriented substantially parallel. Illustratively, the insertion member 74 comprises a plate formed of a rigid material, such as a metal, for example, aluminum.

For mounting the insertion member 74 on the second mounting structure, a first mounting hole 84 is formed in the plate of the insertion member and a second mounting hole 85 is formed in the plate of the insertion member. The first 84 and second 85 mounting holes may be located on a line extending between a midpoint of the upper 78 and lower 79 ends of the insertion member.

The second mounting structure is attached to the insertion member for mounting the insertion member on a medical accessory. Optionally, the second mounting structure may comprise a post structure 90 for supporting a bag (see FIG. 2). The post structure 90 comprises a linking member 92 mounted on the rear face 83 of the insertion member. A post member 94 has upper 95 and lower 96 ends. The post member 94 is mounted on the linking member 92 at the lower end 97 of the post member. The post member 94 extends substantially parallel to a central axis of the insertion member that extends between the upper and lower ends of the insertion member. Significantly, the post member may be gripped by medical devices designed for gripping onto an IV support post for supporting the medical device.

Figure 3:
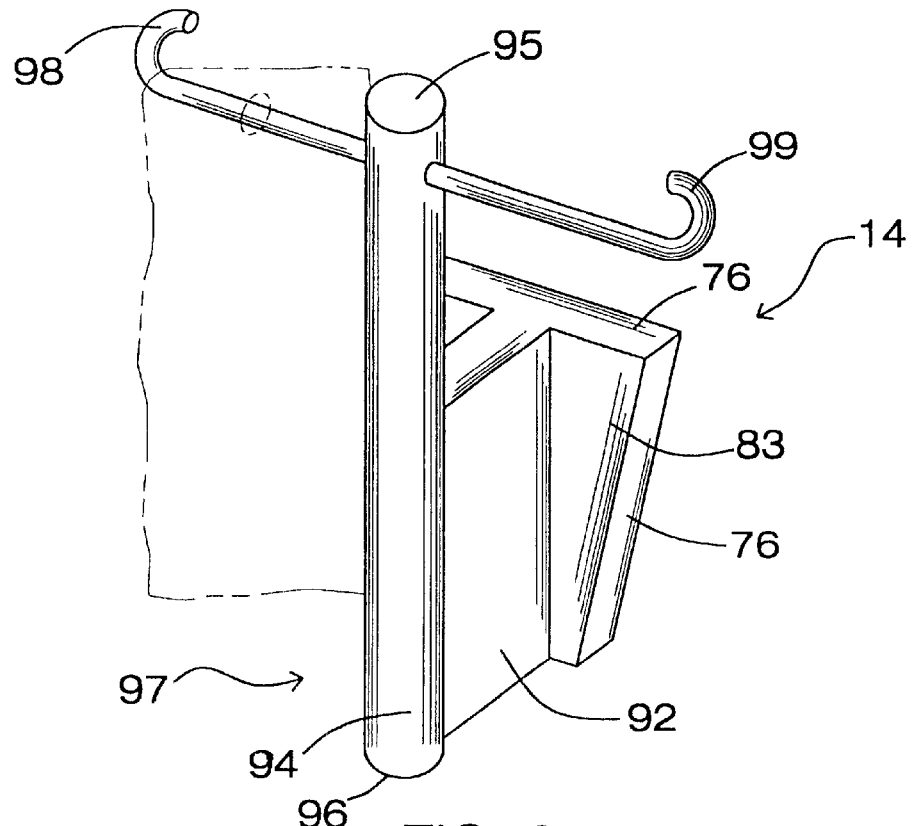
FIG. 3 is a schematic perspective view of one aspect of the male mounting component of the present invention having the insertion member combined with the hanger structure.

An optional variation of the post structure 90 is a bag hanger structure 97 which is similar to the post structure but has an elongated post member for supporting, for example, IV fluid bags in a raised position (see FIG. 3). Preferably, at least one hook member 98 may be mounted adjacent the upper end 96 of the post member 94. The hook member 98 extends substantially perpendicularly to the longitudinal axis of the post member 94. A pair of hook members 94, 99 are preferably included, and each of the pair of hook members extends in a direction substantially opposite of the other hook member. Significantly, a medical accessory such as a fluid pump may be mounted on the post member, and another medical accessory, such as a fluid bag, may be suspended from one or both of the hook members so that a plurality of devices are simultaneously supported.

Figure 8:
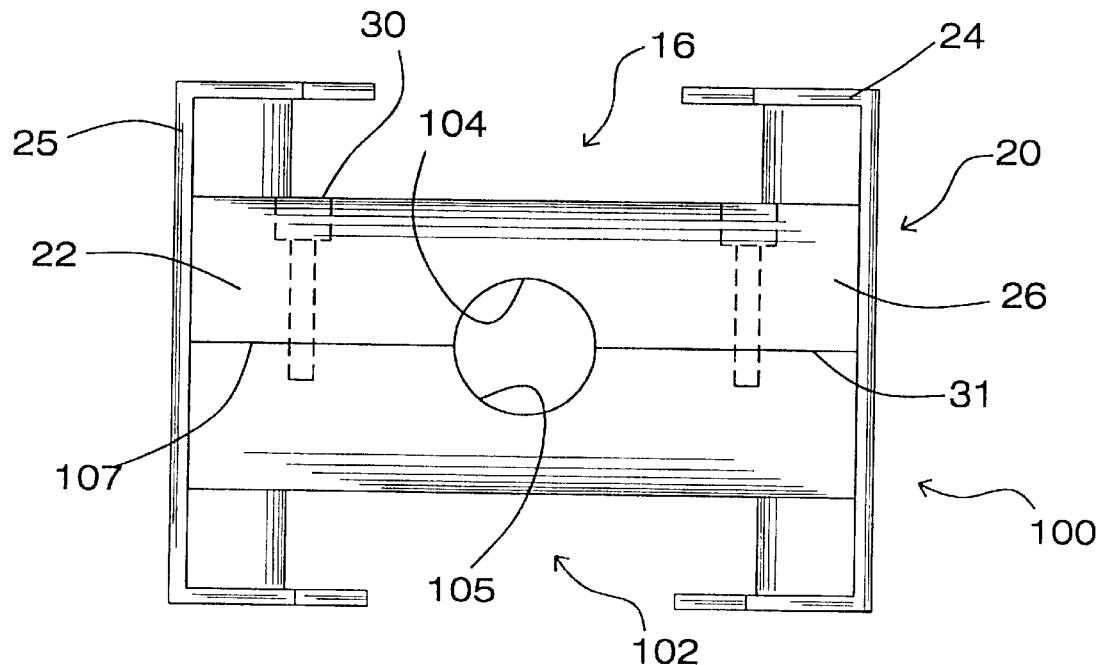
FIG. 8 is a schematic top view of two receiver assemblies coupled together and forming a channel for receiving a bar.

Optionally, a pair of the receiver assemblies 20, 100 are coupled together such that the receptive channels 16, 102 of the receiver assemblies are oriented in opposite directions (see FIG. 8). A channel 104, 105 is formed in each of the rear faces 31, 107 of each of the base members 22, 109 of the receiver assemblies. The rear faces 31, 107 are positioned in an opposed relationship such that the channels 104, 105 are aligned in a parallel relationship to form a generally cylindrical space between the base members for receiving a shaft or bar of a supportive structure. Each of the base members 22, 109 has at least one hole formed therein. The hole in a first one of the base members is alignable with the hole in a second one of the base members. Preferably, a pair of holes are formed in each of the base members, with a fastener being extended through each one of the holes in one of the base members and into a second one of the base members for securing the base members together.

For facilitating easy and quick insertion and removal of the insertion member of the male mounting component, the front face 30 of the base member 22 and the inner surfaces 40, 41 of the channel members are substantially planar and smooth, and the rear face 83 and the substantially straight sides 80, 81 of the insertion member are also substantially planer and smooth so that there is minimal resistance to movement of the insertion member in the receptive channel without significant resistance. Preferably, the weight of the insertion member, the second mounting structure, and the supported medical accessory and the length of the receptive channel between the upper and lower ends is sufficient to resist unintentional removal of the insertion member and retains the insertion member in the receptive channel. Illustratively, the length of the receptive channel is at least approximately 2.5 inches long, but does not exceed approximately 5 inches. The width of the receptive channel is relatively narrow with respect to the length of the channel, and illustratively the width is approximately 1 inch to approximately 2 inches.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A system of interchangeable mountings for removably mounting a medical accessory on a supportive structure, the system comprising:
    a female mounting component for mounting to a supportive structure, the female mounting component comprising:
        a receiver assembly defining a receptive channel, the receiver assembly including a base member and a pair of opposed channel members mounted on the base member to form the receptive channel, the receptive channel having an upper end and a lower end, the receptive channel having a transverse dimension that decreases from the upper end of the receptive channel toward the lower end of the receptive channel; and
        a first mounting structure on the receiver assembly for mounting the receiver assembly on a supportive structure; and
    a male mounting component for mounting to a medical accessory, the male mounting component comprising:
        an insertion member removably insertable into the receptive channel of the female mounting component at the upper end thereof, the insertion member having an upper end and a lower end, the upper end and the lower end each having a transverse dimension that decreases from the upper end toward the lower end; and
        a second mounting structure on the insertion member for mounting the insertion member on a medical accessory; and
    wherein a pair of the receiver assemblies are coupled together such that the receptive channels of the receiver assemblies are oriented in opposite directions.

2. The system of claim 1 additionally comprising a channel being formed in the rear faces of each of the base members of the receiver assemblies, the rear faces being positioned in an opposed relationship such that the channels are aligned in a parallel relationship to form a generally cylindrical space between the base members for receiving a bar of a supportive structure.

3. The system of claim 2 additionally comprising a pair of fasteners, each of the fasteners being extended through both of the base members to connect the base members together, one of the fasteners being located on each side of the channels of the base members.

4. A system of interchangeable mountings for removably mounting a medical accessory on a supportive structure, the system comprising:
    a female mounting component for mounting to a supportive structure, the female mounting component comprising:
        a receiver assembly defining a receptive channel, the receiver assembly including a base member and a pair of opposed channel members mounted on the base member to form the receptive channel, the receptive channel having an upper end and a lower end, the receptive channel having a transverse dimension that decreases from the upper end of the receptive channel toward the lower end of the receptive channel; and
        a first mounting structure on the receiver assembly for mounting the receiver assembly on a supportive structure; and
    a male mounting component for mounting to a medical accessory, the male mounting component comprising:
        an insertion member removably insertable into the receptive channel of the female mounting component at the upper end thereof, the insertion member having an upper end and a lower end, the upper end and the lower end each having a transverse dimension that decreases from the upper end toward the lower end; and
        a second mounting structure on the insertion member for mounting the insertion member on a medical accessory;
    wherein the first mounting structure comprises a bracket mounting structure for mounting the receiver assembly to a bar supportive structure, the bracket mounting structure comprising an inner member and an outer member, the inner member being mounted on the rear face of the base member, the inner and outer members each having an inner face, the inner face of the inner member being oriented toward the inner face of the outer member, the inner faces of the inner and outer members each having a channel formed thereon in an opposed relationship to each other to form a passage therebetween for receiving a bar, the inner faces of the inner and outer members being movable toward and away from each other to thereby move the channels toward and away from each other and adjust a size of the passage for selectively gripping and releasing the bar.

5. The system of claim 4 wherein the inner faces of the inner and outer members each have a portion thereof being formed in the shape of an exterior surface of a cylinder for abutting against an exterior surface of the bar.

6. The system of claim 1 wherein the outer member is mounted on the inner member by a fastening structure, the fastening structure permitting adjustment of the distance between the inner and outer members for adjusting the size of the passage.

7. A system of interchangeable mountings for removably mounting a medical accessory on a supportive structure, the system comprising:

a female mounting component for mounting to a supportive structure, the female mounting component comprising:
  a receiver assembly defining a receptive channel, the receiver assembly including a base member and a pair of opposed channel members mounted on the base member to form the receptive channel, the receptive channel having an upper end and a lower end, the receptive channel having a transverse dimension that decreases from the upper end of the receptive channel toward the lower end of the receptive channel; and
  a first mounting structure on the receiver assembly for mounting the receiver assembly on a supportive structure; and
a male mounting component for mounting to a medical accessory, the male mounting component comprising:
  an insertion member removably insertable into the receptive channel of the female mounting component at the upper end thereof, the insertion member having an upper end and a lower end, the upper end and the lower end each having a transverse dimension that decreases from the upper end toward the lower end; and
  a second mounting structure on the insertion member for mounting the insertion member on a medical accessory;
wherein the first mounting structure comprises a track mounting structure for mounting the receiver assembly to a track, the track comprising a channel with a pair of opposed slots, the track mounting structure comprising an interface plate for mounting to the rear face of the base member, a middle plate mounted on the interface plate, and a slide plate mounted on the middle plate.

8. The system of claim 7 wherein the middle plate has a width less than a width of the slide plate to form a pair of oppositely oriented grooves, the slide plate being adapted to be inserted into and slide along the channel of the track, the slide member having a pair of spaced parallel sides for engaging the opposed slots of the track.

9. A system of interchangeable mountings for removably mounting a medical accessory on a supportive structure, the system comprising: a female mounting component for mounting to a supportive structure, the female mounting component comprising: a receiver assembly defining a receptive channel, the receiver assembly including a base member arid a pair of opposed channel members mounted on the base member to form the receptive channel, the receptive channel having an upper end and a lower end, the receptive channel having a transverse dimension that decreases from the upper end of the receptive channel toward the lower end of the receptive channel; and a first mounting structure mounted on the receiver assembly for mounting the receiver assembly on a supportive structure; and a male mounting component for mounting to a medical accessory, the male mounting component comprising: an insertion member removably insertable into the receptive channel of the female mounting component at the upper end thereof, the insertion member having an upper end and a lower end, the upper end and the lower end each having a transverse dimension that decreases from the upper end toward the lower end; and a second mounting structure mounted on the insertion member for mounting the insertion member on a medical accessory; wherein the base member has an upper end and a lower end, the upper end and the lower end each have a transverse dimension, the transverse dimension of the upper end being greater than the transverse dimension of the lower end, wherein the transverse dimension of the lower end is approximately half of the transverse dimension of the upper end; wherein the base member includes a pair of sides extending between the upper and lower ends, the sides converging toward the lower end and diverging toward the upper end, the sides being substantially straight; wherein the upper and lower ends is substantially straight, the base member having front and rear faces, the front and rear faces each being substantially planar, the front and rear faces being substantially parallel; wherein the base member includes a first mounting hole formed in the insertion member, a second mounting hole formed in the insertion member, the first and second mounting holes being located on a line extending between the upper and lower ends of the base member; wherein the insertion member has a pair of sides extending between the upper and lower ends, the sides converging toward the lower end and diverging toward the upper end, the sides being substantially straight, the upper and lower ends being substantially straight; wherein the transverse dimension of the lower end is approximately half of the transverse dimension of the upper end; wherein the insertion member has front and rear faces, the front and rear faces each being substantially planar, the front and rear faces being substantially parallel; wherein the insertion member includes a first mounting hole formed in the insertion member and a second mounting hole formed in the insertion member, the first and second mounting holes being located on a line extending between the upper and lower ends of the insertion member; wherein the channel members are each mounted on one of the sides of the base member, each of the channel members having a first arm mounted on the side of the base member and a second arm extending substantially parallel to the front face of the base member, the first arm being oriented substantially perpendicular to the second arm, the second arm being spaced from the front face of the base member; wherein the second arm of a first one of the channel members is spaced from the second arm of a second one of the channel members, the second arms of the channel members converging toward each other toward the lower end of the base member to form the receptive channel; and wherein the second arms each have an inward edge, the inward edge of the second arms being substantially linear, the first arms of the channel members each having inner surfaces, the inner surfaces being substantially planar.

* * * * *